United States Patent [19]
Lopez et al.

[11] Patent Number: 5,972,032
[45] Date of Patent: Oct. 26, 1999

[54] ACETABULAR SHELL HAVING FLARED RIM AND FIXATION SPIKES

[75] Inventors: Jorge Lopez, Oxnard, Calif.; Aaron Hofmann, Salt Lake City, Utah

[73] Assignee: Sulzer Orthopedics Inc., Austin, Tex.

[21] Appl. No.: 08/985,637

[22] Filed: Dec. 5, 1997

[51] Int. Cl.⁶ .................................................. A61F 2/34
[52] U.S. Cl. ............................................................. 623/22
[58] Field of Search ............................. 623/16, 18, 19, 623/22, 23

[56] References Cited

U.S. PATENT DOCUMENTS

| | | | |
|---|---|---|---|
| 3,840,904 | 10/1974 | Tronzo | 623/22 |
| 4,173,797 | 11/1979 | Langlais et al. | 623/22 |
| 4,566,138 | 1/1986 | Lewis et al. | 623/22 |
| 4,695,282 | 9/1987 | Forte et al. | 623/22 |
| 4,778,473 | 10/1988 | Matthews et al. | 623/22 |
| 4,892,549 | 1/1990 | Figgie, III et al. | 623/22 |
| 5,108,446 | 4/1992 | Wagner et al. | 623/22 |
| 5,171,287 | 12/1992 | Willert et al. | 623/22 |
| 5,358,532 | 10/1994 | Evans et al. | 623/22 |
| 5,443,519 | 8/1995 | Averill et al. | 623/22 |
| 5,549,698 | 8/1996 | Averill et al. | 623/22 |
| 5,676,704 | 10/1997 | Ries et al. | 623/22 |
| 5,782,928 | 7/1998 | Ries et al. | 623/22 |

*Primary Examiner*—David J. Isabella
*Attorney, Agent, or Firm*—Philip S. Lyren; Kenneth S. Barrow

[57] ABSTRACT

An acetabular component for an implantable hip joint prosthesis. An acetabular shell has an apex and a rim, and has a convex proximal surface for being received within a hemispherically reamed acetabulum in a press-fit relationship. The convex proximal surface is shaped as a surface of revolution defined by a curve segment rotated about an axis, where the curve segment and the axis lie in a common plane. The defining curve segment includes a first arc-segment and a second arc-segment. The first arc-segment has a center located on the axis, and the second arc-segment has a center offset from the axis. The convex proximal surface includes a first region defined by the first arc-segment in proximity to the apex and a second region defined by the second arc-segment in proximity to the rim. The convex proximal surface is diametrically oversized in the second region relative to the hemispherically reamed acetabulum. At least one bone-penetrating protrusion extends generally proximally from the convex proximal surface, but is limited in proximal extent to remain unengaged with the hemispherically reamed acetabulum at initial contact of the oversized second region with the hemispherically reamed acetabulum during implantation.

37 Claims, 4 Drawing Sheets

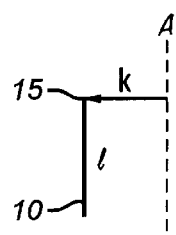
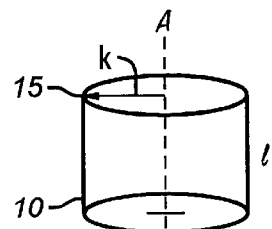
FIG. 1a  FIG. 1b
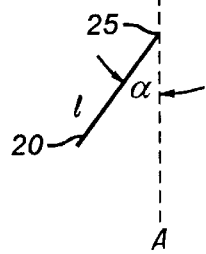
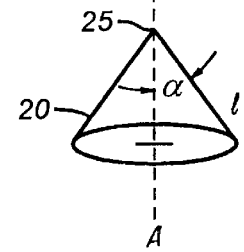
FIG. 2a  FIG. 2b
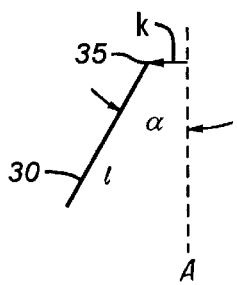
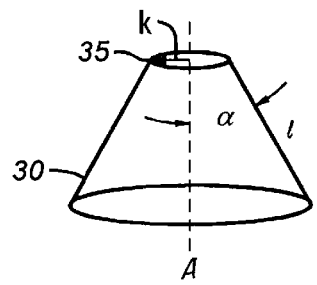
FIG. 3a  FIG. 3b
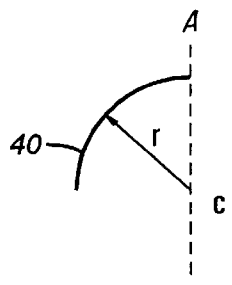
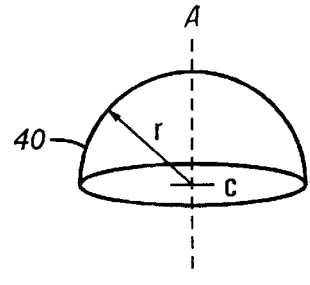
FIG. 4a  FIG. 4b
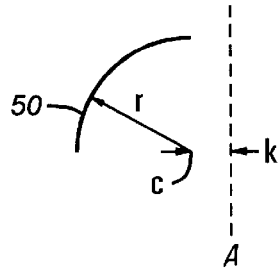
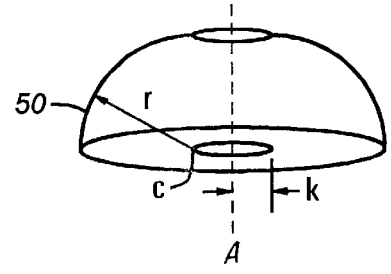
FIG. 5a  FIG. 5b

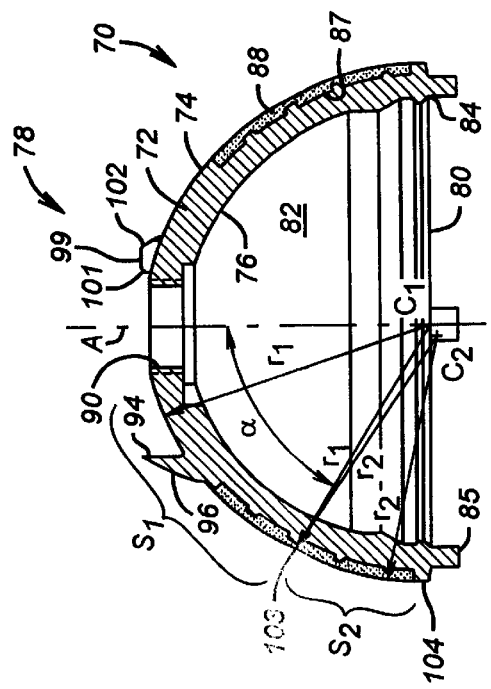
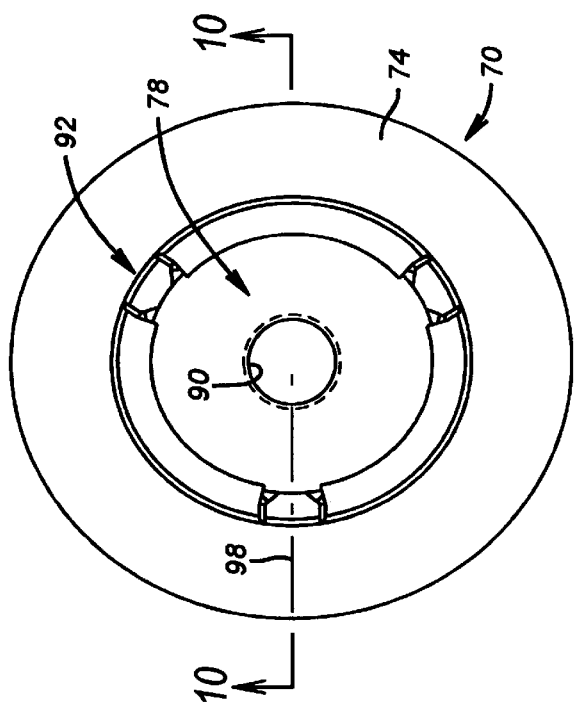
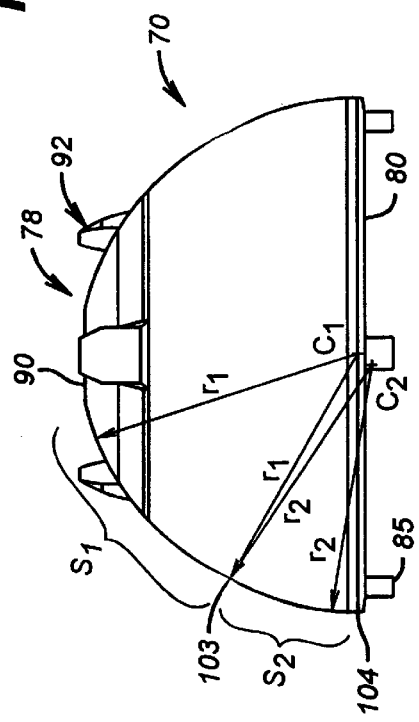

ACETABULAR SHELL HAVING FLARED RIM AND FIXATION SPIKES

BACKGROUND OF THE INVENTION

1. Field of the Invention

The present invention relates generally to implantable prostheses for replacing human skeletal joints, and relates more particularly to an acetabular cup component of a total hip prosthesis.

2. Background Information

An implantable total hip prosthesis includes a femoral component and an acetabular cup component. The femoral component, typically made of a bio-compatible metal such as titanium, titanium alloy or cobalt chrome alloy, has a distal stem and a proximal spherical head. As used herein, the words proximal and distal are terms of reference that indicate a particular portion of a prosthesis component according to the relative disposition of the portion when the component is implanted. "Proximal" indicates that portion of a component nearest to the torso, whereas "distal" indicates that portion of the component farthest from the torso. The distal stem is configured to be received and fixed within the medullary canal of a femur. The femur is prepared to receive the distal stem by resecting the natural head and neck, and reaming the exposed proximal medullary canal. The proximal end of the femoral component has a neck and attached spherical head that, supported by the distal stem anchored in the medullary canal, extend from the resected proximal end of the femur to replace the natural neck and head of the proximal femur. The proximal spherical head may be integral with the neck and stem of the femoral component, or may be removably attachable to the neck by way of a locking taper connection, sometimes known as a Morse taper. The acetabular cup component is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball and socket to restore motion to a defective hip joint.

One known type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component.

Acetabular shells of the type described can be affixed to the acetabular bone by means of bone screws, bone cement, bone ingrowth or ongrowth, mechanical interference, or by a combination of two or more of these means. To promote bone ingrowth or ongrowth, the convex proximal surface of an acetabular shell, i.e., the bone-engaging surface, can be provided with a porous coating applied as sintered metal particles, spheres, or wire mesh, or as plasma sprayed metal, for example. In lieu of porous coating, the bone-engaging surface can be roughened by grit blasting. As an option, the porous or grit blasted surface can be coated with hydroxylapatite, applied by plasma spraying, to further enhance the osseoinductive characteristics of the acetabular shell. Fixation by mechanical interference can be accomplished by carefully reaming the acetabulum to a contour that, in combination with the contour of the proximal bone-engaging surface of the acetabular shell, results in a press-fit relationship between the acetabular shell and the acetabular bone. Also, gross mechanical interference between shell and bone can be accomplished by means of sharp protrusions on the bone-engaging surface of the acetabular shell, such as threads, grooves, fins, spikes, or other macro-textured surface features that penetrate into the acetabular bone as the shell is implanted.

Some acetabular shells that employ a press-fit relationship between the acetabular shell and the acetabular bone rely upon the acetabular shell being somewhat oversized in diameter relative to the diameter of the reamed acetabulum. Some such designs extend the oversized area well away from the rim of the cup, which can result in compressive forces being generated in the acetabular bone that have a significant axial component. This can lead to a risk of the acetabular cup being expelled from the acetabulum, incomplete seating and or fracture of the acetabulum. It would be desirable to provide an acetabular shell, designed to optimize a press-fit relationship to acetabular bone, that attempts to alleviate the forementioned risks. The present invention provides this and other desirable advantages.

Many acetabular shells that exploit gross mechanical interference with the bone to achieve fixation or stabilization can be somewhat difficult to orient accurately during implantation. This is because the protrusions that effect fixation must necessarily engage the bone before the main body of the acetabular shell engages the bone, resulting in the protrusions being committed to a particular path of penetration into the bone before the cup body has been assuredly positioned within the reamed acetabulum. It would be desirable to provide an acetabular shell, designed to employ mechanical fixation to bone, that can be oriented accurately in the reamed acetabulum before being driven into its fully seated position. The present invention provides this and other desirable advantages.

SUMMARY OF THE INVENTION

According to one aspect of the present invention, an acetabular component for an implantable hip joint prosthesis includes an acetabular shell having a convex proximal surface comprising a surface of revolution defined by a curve segment lying in a plane, and an axis lying in the plane, where the curve segment is rotated about the axis. The curve segment includes a first portion including an arc-segment having a first radius and a second portion including an arc-segment having a second radius. The arc-segment of the first portion has a center located on the axis. The arc-segment of the second portion has a center offset from the axis.

According to another aspect of the present invention, an acetabular component for an implantable hip joint prosthesis includes an acetabular shell having a convex proximal surface having at least one bone-penetrating protrusion extending generally proximally therefrom. The convex proximal surface has a rim portion that is oversized in diameter relative to a hemispherical bone cavity into which the acetabular shell is designed to be received in press-fit relationship. The axial extent of the bone-penetrating protrusion is limited such that the oversized rim portion contacts the hemispherical bone cavity in line contact before the bone-penetrating protrusion engages the bone as the acetabular shell is implanted into the hemispherical bone cavity.

It is an object of the present invention to provide an improved acetabular hip prosthesis.

Other objects and advantages of the present invention will be apparent from the following descriptions of the preferred embodiment illustrated in the drawings.

BRIEF DESCRIPTION OF THE DRAWINGS

FIGS. 1a–7b are schematic representations of geometric concepts useful for understanding the present invention.

FIG. 8 is an elevation view of an acetabular shell constructed in accordance with the present invention.

FIG. 9 is a top view of the acetabular shell of FIG. 8.

FIG. 10 is cross-sectional view of the acetabular shell of FIG. 8, taken in plane 10—10 of FIG. 9 and viewed in the direction of the arrows.

DESCRIPTION OF THE PREFERRED EMBODIMENT

Figure 6:
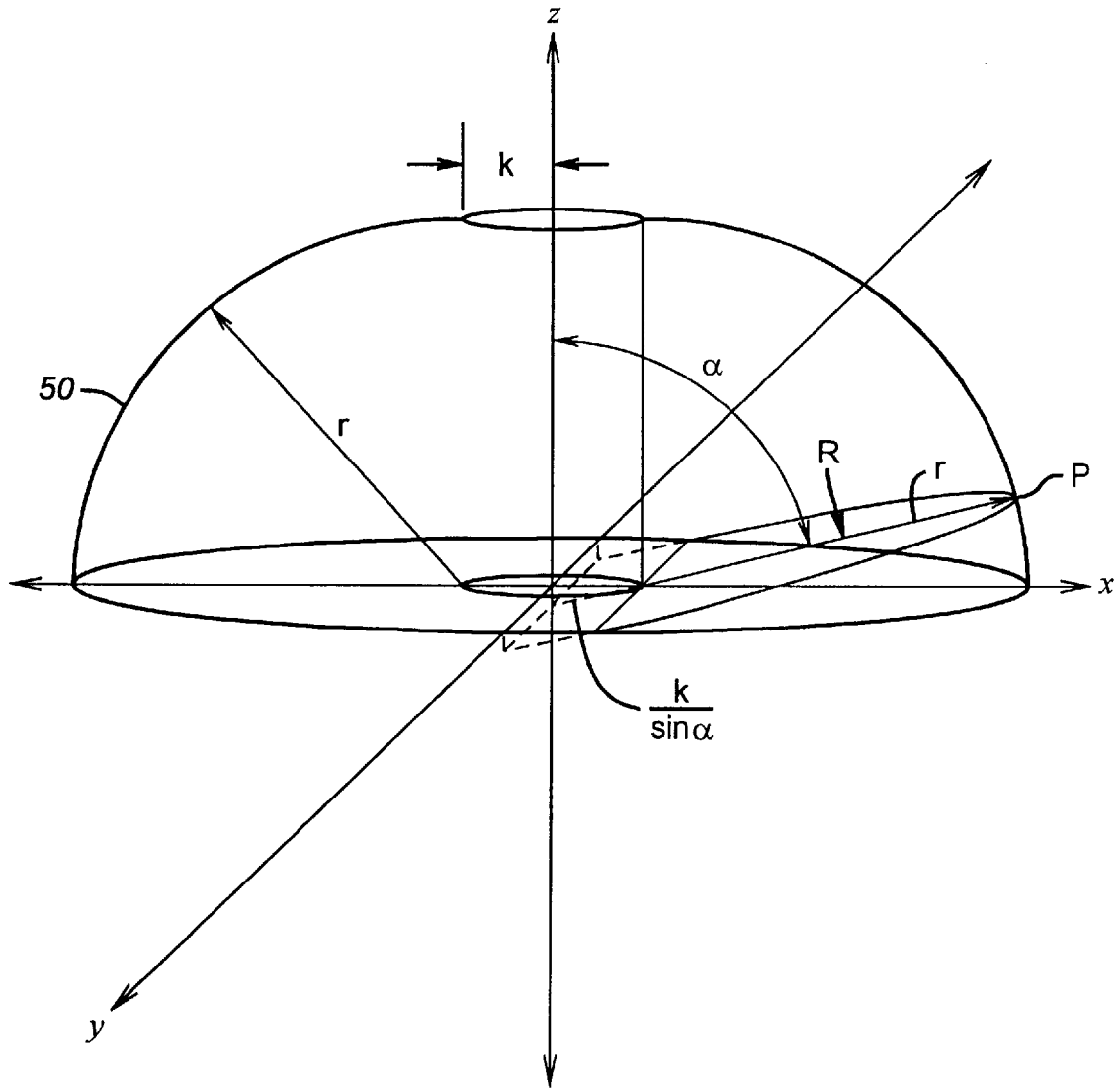

An acetabular shell, in accordance with the present invention, includes a three-dimensional, generally convex outer surface that can be described as a surface of revolution. More particularly, the outer surface is a surface of revolution generated by revolving a plane curve segment through 360° about an axis lying in the plane of the curve. By defining the shape of the curve segment, and the orientation and location of the curve segment relative to the axis, the three-dimensional surface of revolution can be specified. By way of introduction, simple surfaces of revolution are illustrated in FIGS. 1a–5b.

In FIG. 1a, a line segment 10 of length l lies parallel to axis A and has an endpoint 15 that is offset perpendicularly from axis A by a non-zero distance k. By revolving line segment 10 through 360° about axis A, a right cylindrical surface of revolution is generated, as illustrated in the perspective view of FIG. 1b.

In FIG. 2a, a line segment 20 of length l is coplanar with and lies at an acute angle $\alpha$ to axis A, and has an endpoint 25 that lies on axis A. By revolving line 20 through 360° about axis A, a right conical surface of revolution is generated, as illustrated in the perspective view of FIG. 2b.

In FIG. 3a, a line segment 30 of length l is coplanar with and lies at an acute angle $\alpha$ to axis A, and has an endpoint 35 that is offset perpendicularly from axis A by a non-zero distance k. By revolving line segment 30 through 360° about axis A, a truncated right conical surface of revolution is generated, as illustrated in the perspective view of FIG. 3b.

In FIG. 4a, an arc segment 40 of radius r, subtending an angle of 90°, is coplanar with and has a center c that lies on axis A. By revolving arc segment 40 through 360° about axis A, a right hemispherical surface of revolution is generated, as illustrated in the perspective view of FIG. 4b.

In FIG. 5a, an arc segment 50 of radius r, subtending an angle of 90°, is coplanar with and has a center c that is offset by a non-zero distance k from axis A. By revolving arc segment 50 through 360° about axis A, an arc-cylindrical surface of revolution is generated, as illustrated in the perspective view of FIG. 5b. The resulting three-dimensional surface, although generated by an arc segment swept in a circular path about an axis, is not spherical in curvature. This is explained further below with respect to FIG. 6.

In FIG. 6, the three-dimensional surface of FIG. 5b is reproduced against a frame of reference comprising three mutually orthogonal axes x, y and z. The radius of curvature of the surface at a selected point p is defined by a vector normal to the surface, having a length R. The length R can vary with the angular displacement $\alpha$ of the selected point p, relative to the z axis. The length R also can vary with the orientation of the plane in which the curvature is to be determined, that plane necessarily including the normal vector. In one simple case the plane of interest is oriented coplanar with the plane of the defining arc-segment 50, i.e., the plane of interest is defined by axes x and z. In that simple case, R=r, regardless of the angle $\alpha$. A more interesting case is where the plane of interest is perpendicular to the plane of the defining arc-segment 50. In the latter case, the radius of curvature, R, at a selected point on the surface p, is r plus a projected extension of the normal vector onto axis z. The projected extension is equal to k/sin $\alpha$, where $\alpha$ is the acute angle between the normal vector and axis z. At one extreme, where the selected point on the surface is displaced from axis z at an angle $\alpha$=90° and the plane of interest lies perpendicular to the plane of the defining arc-segment 50, the radius of curvature, R, is r+(k/sin 90°)=r+k. At another extreme, where the selected point on the surface is displaced from axis z at angle $\alpha$=0° and the plane of interest lies perpendicular to the plane of the defining arc-segment 50, the radius of curvature, R, is r+k/sin 0°=r+$\infty$. In general, the radius of curvature, R, at any arbitrary point on the three-dimensional surface and in any selected plane of interest will vary between the limits of r to $\infty$.

Figure 7A:
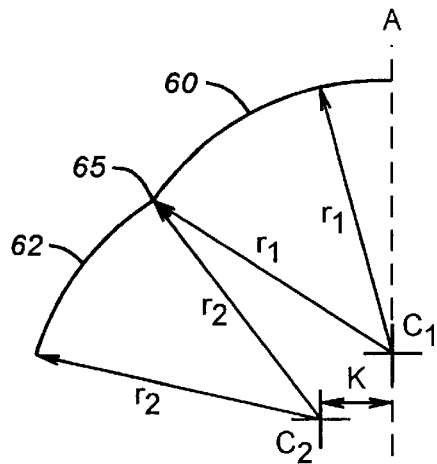
Figure 7B:
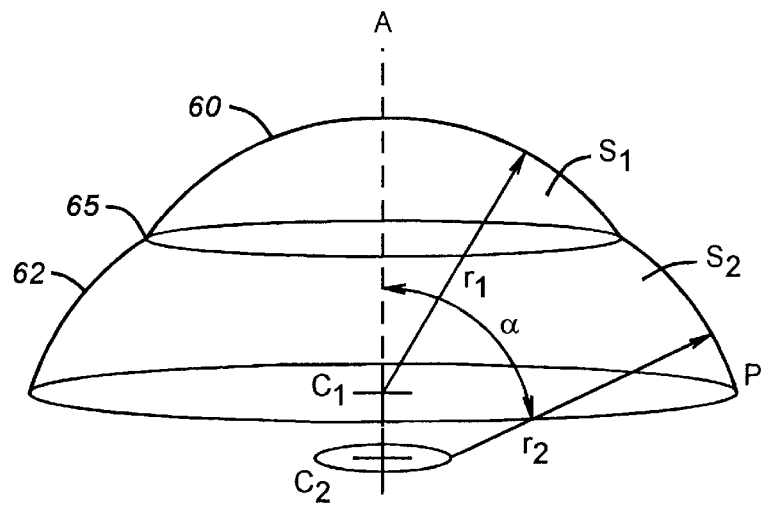

Referring to FIGS. 7a and 7b, an arc-segment 60 of radius r1, subtending an angle of about 45°, is coplanar with and has a center c1 on axis A. An arc-segment 62 of radius r2, subtending an angle of about 35°, is coplanar with arc-segment 60 and has a center c2 offset from axis A by a non-zero distance k. Center c2 is also offset distally relative to center c1. Arc-segment 60 and arc-segment 62 join at a mutual end-point 65. By revolving arc-segment 60 and arc-segment 62 together through 360° about axis A, a complex three-dimensional surface of revolution is generated, as illustrated in the perspective view of FIG. 7b. The resulting three-dimensional surface includes a first region S1 and a second region S2. First region S1 has a curvature substantially similar to that described above with respect to FIGS. 4a and 4b, whereas second region S2 has a curvature substantially similar to that described above with respect to FIGS. 5a, 5b and 6.

First region S1 is spherically curved, defined by a radius of curvature r1 having a center at c1 located on the axis of symmetry A, whereas second region S2 is non-spherically curved. The surface in second region S2 is defined in the axial plane by a radius of curvature r2, equal to r1, having a center c2 located on a circular locus-of-points, c2. Center c2 is offset radially from axis A by a distance k. To maintain r2 equal to r1 at the transition from first region S1 to second region S2 at location 72, center c2 is offset distally from center c1 by an appropriate distance. For any selected point p on the surface in region S2, the radius of curvature can vary between the limits of r2 (equal to r1) and ∞, as discussed above with respect to FIG. 6, depending on the angular displacement α of point p relative to axis A, and depending upon the orientation of the plane in which the curvature is to be determined.

Referring to the drawings, FIGS. 8–10, a preferred embodiment of the present invention is illustrated and described with occasional reference to the introductory principles discussed above. The preferred embodiment is in the form of an implantable orthopedic prosthesis, particularly an acetabular shell component of a total hip joint prosthesis. The illustrated acetabular shell is useful as one component of that well-known type of total hip joint prosthesis that includes an acetabular shell and an associated bearing liner, and a femoral stem and an associated spherical head. The spherical head, fixed to the femoral stem, articulates in a ball-and-socket arrangement within the bearing liner, with the bearing liner being essentially fixed within the acetabular shell. The femoral stem and acetabular shell are fixed to bone of the proximal femur and pelvic acetabulum, respectively. Only the acetabular shell is described in detail herein, as the various types and configurations of bearing liners and the means for affixing such bearing liners within an acetabular shell are well understood in the art. The illustrated acetabular shell is particularly advantageous for non-cemented implantation, but the utility of the invention is not necessarily diminished by the use of bone cement.

Acetabular shell 70 is shaped generally as a hollow cup having a shell wall 72 defined by a convex proximal surface 74 and a concave distal surface 76. Acetabular shell 70 has a proximal dome region 78 at the apex of shell wall 72 and an annular rim 80 at the distal end of shell wall 72. Concave distal surface 76 of shell wall 72 defines a shell cavity 82 having an opening 84 into and through which a bearing insert (not shown) can be received. The preferred bearing insert is made of ultra high molecular weight polyethylene and has a partially spherical bearing cavity that opens distally for receiving a spherical head of a femoral component (not shown) in a ball-and-socket articulating relationship. A means, comprising an annular protrusion on the bearing insert, is preferred for affixing the bearing insert against axial displacement within shell cavity 82. Such means also includes an annular flange, having circumferentially spaced notches, that engages rim 80. Legs 85, which extend axially from rim 80, are received within the notches of the annular flange of the bearing insert to affix the insert against rotational displacement within shell cavity 82. Shell wall 82 is generally symmetrical about an axis A that passes through the center of proximal dome region 78 at the apex of shell wall 72. Convex proximal surface 74 is provided with a macro-texture comprising grooves 87, filled and covered by a porous coating layer 88. Porous coating layer 88 comprises sintered titanium particles, providing a rough and porous surface that mechanically engages bone, and accepts ingrowth or ongrowth of bone. Although the use of bone cement is not preferred with disclosed embodiment, porous coating layer 88 is compatible with and capable of enhancing adhesion of bone cement. Such surface features are well known in the art.

Acetabular shell 70 includes a dome hole 90 centered at the apex of dome region 78 in coaxial alignment with axis A. Dome hole 90 has a substantially cylindrical side wall that is, preferably, internally threaded or otherwise configured to serve as an engagement interface for an instrument (not shown) for holding and positioning acetabular shell 70. Typically, such an instrument is used by the implanting physician to securely grasp the acetabular shell and place it in the reamed acetabulum. Such an instrument usually includes an elongate handle for controlling anteversion and adduction of the acetabular shell as it is implanted, and for transmitting axial driving forces to the shell.

Adjacent the dome region 78, and circumferentially evenly spaced about dome hole 90, are three spikes 92 that extend generally axially from convex proximal surface 74. Each of spikes 92 includes a planar inner surface 94 and a planar outer surface 96. Inner and outer surfaces 94 and 96 are disposed generally perpendicular to a plane defined by axis A and a radius 98 bisecting spike 92. Inner and outer surfaces 94 and 96 converge in the axially proximal direction and meet to define a sharp edge 99. Inner surface 94 slopes radially outwardly and proximally at a small acute angle relative to axis A. Outer surface 96 slopes radially inwardly and proximally at an acute angle somewhat larger than that of inner surface 94. These surfaces aid in resisting tilting and rotation about axis A. See FIGS. 9 and 10. As viewed in the radial direction, each spike 92 is beveled, or "dog-eared" at the circumferential ends of edge 99, resulting in bevel surfaces 101 and 102. Overall, each spike 92 is a proximally pointing wedge of relatively small included angle, sufficiently sharp to readily penetrate acetabular bone as acetabular shell 70 is seated in the reamed, prepared acetabulum. Spikes 92, when so penetrated within acetabular bone, prevent acetabular shell 70 from becoming displaced by rotation relative to the acetabulum. Rotation about axis A and also rotation about any axis perpendicular to axis A are prevented by the engagement of spikes 92 in acetabular bone.

Convex proximal surface 74 is generally spherical in curvature in a first region S1 from dome hole 90 to a location 103 between dome hole 90 and peripheral edge 104. Location 103 is preferred to be situated at an angle α of about 45° relative to axis A. In a second region S2 between location 103 and peripheral edge 104, proximal surface 74 is non spherical, in that the radius of curvature of surface 74 in that region differs depending on the orientation of the plane in which curvature is to be determined. In general, proximal surface 74 flares radially outwardly in the distal direction, relative to an imaginary hemispherical distal extension of the first spherical region S1 of surface 74. The maximum flare diameter occurs at peripheral edge 104, and is preferred to be about 0.5 to 1.0 mm in excess of the corresponding diameter of the imaginary hemispherical distal extension of the first spherical portion S1. The curvature of surface 74 in second region S2 is substantially that of the geometry described above with respect to FIGS. 7a and 7b, and that former description applies to the embodiment of FIGS. 8–10 to the extent of the geometric parameters indicated by the common reference symbols c1, c2, r1, r2, S1 and S2.

Figure 11:
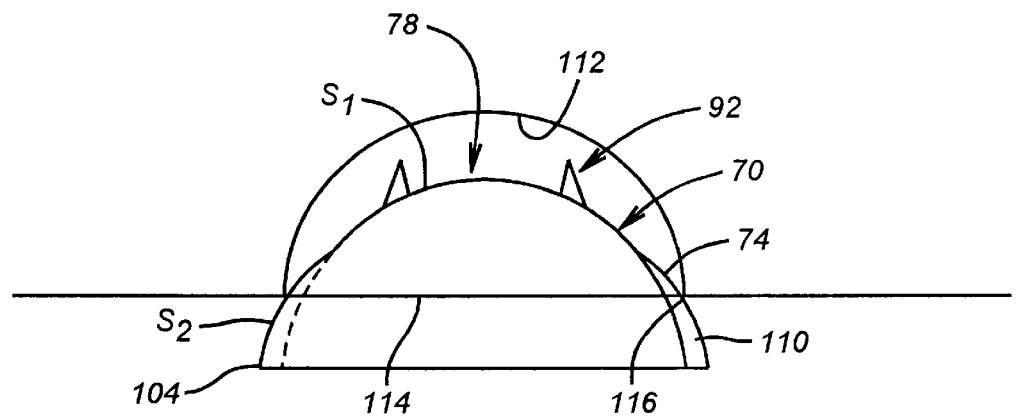
FIG. 11 is a schematic representation of the acetabular shell of FIG. 8 illustrating the geometry of the proximal surface of the shell in relationship to a hemispherically reamed acetabulum.

Referring now to FIG. 11, there is illustrated, in schematic form, a further aspect of the geometry of the preferred embodiment of FIGS. 8–10. Because region S2 of surface 74 departs from an imaginary hemispherical extension of spherical region S1 of surface 74, resulting in a flare at peripheral edge 104, it naturally follows that the preferred embodiment of an acetabular shell will encounter interference with acetabular bone at peripheral edge 104 if pressed into an acetabulum that has had a hemispherical cavity reamed therein to match the radius of curvature of first region S1. Indeed, such an interference fit is the preferred manner of implanting the acetabular shell of the present invention. As shown in FIG. 11, greatly exaggerated, a wedge-shaped cross-sectional area of interference 110, which reaches a maximum at peripheral edge 104, assures a tight press fit retention of the acetabular shell 70 in the reamed acetabulum. Because the degree of interference increases toward and is concentrated near the rim, the resulting compressive forces acting on the acetabular shell have a radially-directed component that is significantly greater than any axially-directed component. As a result, the stress in the bone is primarily hoop stress, directed perpendicular to the axis of the acetabular shell. Consequently, there is little tendency for compressive forces in the bone to expel the acetabular cup from the reamed cavity. Any expulsive forces that may exist are overcome by the large frictional forces generated at the peripheral edge 104.

A further consequence of the flared rim of the acetabular shell of the present invention is that initial contact between the shell and the hemispherically reamed acetabular bone occurs in the form of line contact within region S2 of surface 74. At first contact, the apex or dome region 78 of the acetabular shell remains suspended in spaced relationship to the apex of the hemispherically reamed acetabulum. The present invention exploits this phenomenon by providing that the location and length of the spikes 92 are selected such that line contact occurs between the opening of the reamed acetabulum and region S2 of surface 74 before any contact occurs between spikes 92 and acetabular bone. The line contact provides a centering, or piloting action, assuring that the acetabular shell is centered within the reamed acetabulum before the spikes are driven into the acetabular bone. A certain amount of anteversion and adduction correction can be performed with the acetabular shell remaining only in line contact with the acetabulum before the physician commits to driving the shell into its fully seated position.

The present invention has been illustrated and described with particularity in terms of a preferred embodiment. Nevertheless, it should be understood that no limitation of the scope of the invention is intended thereby. The scope of the invention is defined by the claims appended hereto. It should also be understood that variations of the particular embodiment described herein, incorporating the principles of the present invention, will occur to those of ordinary skill in the art and yet be within the scope of the appended claims.

We claim:

1. An acetabular component for an implantable hip joint prosthesis comprising:

an acetabular shell having an oversized convex proximal surface for being received within a hemispherically reamed acetabulum in a press-fit relationship, said convex proximal surface being shaped as a surface of revolution defined by a curve segment rotated about an axis, said curve segment and said axis lying in a common plane;

said curve segment including a first arc-segment and a second arc segment, said first arc segment having a first center located on said axis, and said second arc-segment having a second center offset from said axis;

said convex proximal surface including a spherically curved first region defined by said first arc-segment and a substantially nonspherically curved second region defined by said second arc-segment; and at least one bone penetrating protrusion extending generally proximally from said convex proximal surface, said bone penetrating protrusion being limited in proximal extent to remain unengaged with the hemispherically reamed acetabulum at initial contact of said proximal surface within the hemispherically reamed acetabulum during implantation.

2. The acetabular component of claim 1, in which said second center is offset transversely from said axis by about 0.5 mm.

3. The acetabular component of claim 1, in which said first arc-segment has a first radius and said second arc-segment has a second radius.

4. The acetabular component of claim 3, in which said first radius and said second radius are substantially equal.

5. The acetabular component of claim 4, in which said second center is offset transversely from said axis by about 0.5 mm.

6. The acetabular component of claim 1, in which said convex proximal surface includes a first region defined by said first arc-segment and a second region defined by said second arc-segment, said first region protruding from said second region.

7. The acetabular component of claim 6, in which said first arc-segment has a first radius and said second arc-segment has a second radius, said bone penetrating protrusion including a planar inner surface and a planar outer surface, each surface being sloped to converge and define a sharp bone penetrating edge.

8. The acetabular component of claim 7, in which said first radius and said second radius are substantially equal.

9. The acetabular component of claim 6, in which said acetabular shell has an apex and a rim, said first region being disposed in proximity to said apex and said second region being disposed in proximity to said rim.

10. The acetabular component of claim 9, in which said second center is offset transversely from said axis by about 0.5 mm.

11. An acetabular component for an implantable hip joint prosthesis comprising:

an acetabular shell having a convex proximal surface shaped as a surface of revolution defined by a curve segment rotated about an axis, said curve segment and said axis lying in a common plane;

said curve segment including a first arc-segment and a second arc-segment, said first arc-segment having a first center located on said axis, and said second arc-segment having a second center offset from said axis;

said convex proximal surface including a first region defined by said first arc-segment and a second region defined by said second arc-segment, said first region protruding from said second region; and said convex proximal surface in said first region being substantially spherically curved, and said convex proximal surface in said second region being substantially nonspherically curved.

12. The acetabular component of claim 11, in which said acetabular shell has an apex and a rim, said first region being disposed in proximity to said apex and said second region being disposed in proximity to said rim.

13. The acetabular component of claim 11, in which said second center is offset transversely from said axis by about 0.5 mm.

14. The acetabular component of claim 11, in which said first arc-segment has a first radius and said second arc-segment has a second radius.

15. The acetabular component of claim 14, in which said first radius and said second radius are substantially equal.

16. An acetabular component for an implantable hip joint prosthesis comprising:

an acetabular shell including an apex and a rim, and having a convex proximal surface for being received with a hemispherically reamed acetabulum in a press-fit relationship, said convex proximal surface including a spherically curved first region in proximity to said apex and a substantially nonspherically curved second region in proximity to said rim, said convex proximal surface being diametrically oversized in said second region relative to the hemispherically reamed acetabulum; and at least one bone-penetrating protrusion extending generally proximally from said convex proximal surface, said bone-penetrating protrusion being limited in proximal extent to remain unengaged with the hemispherically reamed acetabulum at initial contact of said oversized second region with the hemispherically reamed acetabulum during implantation.

17. An acetabular component for an implantable hip joint prosthesis comprising:

an acetabular shell including an apex and a rim, and having a convex proximal surface for being received within a hemispherically reamed acetabulum in a press-fit relationship, said convex proximal surface including a first region in proximity to said apex and a second region in proximity to said rim, said convex proximal surface being diametrically oversized in said second region relative to the hemispherically reamed acetabulum;

at least one bone-penetrating protrusion extending generally proximally from said convex proximal surface, said bone-penetrating protrusion being limited in proximal extent to remain unengaged with the hemispherically reamed acetabulum at initial contact of said oversized second region with the hemispherically reamed acetabulum during implantation; and said convex proximal surface in said second region being substantially nonspherically curved.

18. The acetabular component of claim 17, in which said convex proximal surface in said first region is substantially spherically curved.

19. The acetabular component of claim 17, in which said convex proximal surface in said second region is shaped as a surface of revolution defined by a second arc-segment rotated about an axis, said second arc-segment and said axis lying in a common plane.

20. The acetabular component of claim 19, in which said second arc-segment of said second region of said convex proximal surface has a second center offset from said axis.

21. The acetabular component of claim 17, in which said convex proximal surface in said first region is shaped as a surface of revolution defined by a first arc-segment rotated about said axis, said first arc-segment lying in a common plane with said second arc-segment and said axis.

22. The acetabular component of claim 21, in which said first arc-segment of said first region of said convex proximal surface has a first center located on said axis.

23. The acetabular component of claim 22, in which said first arc-segment has a first radius and said second arc-segment has a second radius.

24. The acetabular component of claim 23, in which said first radius and said second radius are substantially equal.

25. The acetabular component as defined in claim 16 wherein said bone penetrating protrusion extends from said first region of said convex proximal surface.

26. The acetabular component as defined in claim 16 wherein said bone penetrating protrusion extends from said first region of said convex proximal surface and is positioned adjacent said second region of said convex proximal surface.

27. The acetabular component as defined in claim 16 wherein said bone penetrating protrusion includes a planar inner facing surface and a planar outer facing surface.

28. The acetabular component as defined in claim 27 wherein said inner and outer facing surfaces are sloped to converge and define a sharp bone penetrating edge.

29. The acetabular component as defined in claim 28 wherein said bone penetrating protrusion includes a pair of opposed beveled edges which terminate at said sharp bone penetrating edge.

30. The acetabular component as defined in claim 16 wherein said bone penetrating protrusion is wedge shaped and includes a sharp terminal bone penetrating edge.

31. The acetabular component as defined in claim 30 wherein said bone penetrating protrusion includes opposed, converging planar surfaces for resisting tilting and rotation of said shell.

32. The acetabular component as defined in claim 16 wherein said bone penetrating protrusion is between said apex and said rim, and extends from said first region of said convex proximal surface, and is positioned adjacent said second region of said convex proximal surface.

33. The acetabular component as defined in claim 16 further comprising a plurality of bone penetrating protrusions similar to said bone penetrating protrusion.

34. The acetabular component as defined in claim 33 wherein each of said bone penetrating protrusions include inner and outer facing surfaces, said inner and outer facing surfaces being sloped to converge and define a sharp bone penetrating edge thereon.

35. The acetabular component as defined in claim 34 wherein each of said bone penetrating protrusions includes a pair of opposed beveled edges which terminate at said sharp bone penetrating edge.

36. The acetabular component as defined in claim 33 wherein each of said bone penetrating protrusions include opposed, converging planar surfaces for resisting tilting and rotation of said shell.

37. The acetabular component as defined in claim 33 wherein each of said bone penetrating protrusions is radially spaced apart from each other of said bone penetrating protrusions on said shell between said apex and said rim, each of said bone penetrating protrusions extending from said first region of said convex proximal surface, and being positioned adjacent said second region of said convex proximal surface.

* * * * *